United States Patent [19]

Appelt et al.

[11] Patent Number: 5,618,899
[45] Date of Patent: Apr. 8, 1997

[54] CROSSLINKED PRESSURE-SENSITIVE ADHESIVES TOLERANT OF ALCOHOL-BASED EXCIPIENTS USED IN TRANSDERMAL DELIVERY DEVICES AND METHOD OF PREPARING SAME

[76] Inventors: Marian R. Appelt; Sharon K. Grosh, both of P.O. Box 33427, St. Paul, Minn. 55133-3427

[21] Appl. No.: 454,496

[22] Filed: May 30, 1995

Related U.S. Application Data

[62] Division of Ser. No. 517,927, May 2, 1990.

[51] Int. Cl.$^6$ .............................. C08F 26/08; C08J 3/28; A61F 13/02
[52] U.S. Cl. .................. 526/264; 522/152; 522/153; 522/182; 424/448
[58] Field of Search ................ 424/448; 526/264; 522/152, 113, 182

[56] References Cited

U.S. PATENT DOCUMENTS

| Re. 24,906 | 12/1960 | Ulrich | 206/59 |
|---|---|---|---|
| 2,553,816 | 5/1951 | Ebel | 117/122 |
| 2,925,174 | 2/1960 | Stow | 206/59 |
| 2,956,904 | 10/1960 | Hendricks | 117/93 |
| 2,973,286 | 2/1961 | Ulrich | 117/122 |
| 3,121,021 | 2/1964 | Copeland | 117/122 |
| 3,475,363 | 10/1969 | Gander | 260/29.7 |
| 3,532,652 | 10/1970 | Zang et al. | 260/23 |
| 4,432,848 | 2/1984 | Korpman | 204/159.17 |
| 4,693,776 | 9/1987 | Krampe et al. | 156/327 |
| 4,695,604 | 9/1987 | Amirsakis | 525/28 |
| 4,699,146 | 10/1987 | Sieverding | 128/640 |
| 4,714,655 | 12/1987 | Bordoloi et al. | 428/345 |
| 4,732,808 | 3/1988 | Krampe et al. | 428/355 |
| 4,737,559 | 4/1988 | Kellen et al. | 526/291 |
| 4,750,482 | 6/1988 | Sieverding | 128/156 |
| 5,011,867 | 4/1991 | Mallya et al. | 522/109 |

FOREIGN PATENT DOCUMENTS

| 0068696 | 1/1983 | European Pat. Off. | C09J 3/14 |
|---|---|---|---|
| 1216908 | 12/1970 | United Kingdom | A61I 15/06 |
| 2048274 | 10/1980 | United Kingdom | C09J 7/02 |
| 86/062181 | 11/1986 | WIPO | A61L 15/06 |
| 89/00106 | 12/1989 | WIPO | B32B 5/16 |

OTHER PUBLICATIONS

Tappi Journal, Jun. 1988 (Ewins, Jr. et al.) pp. 155–158.
Chemtech, Sep. 1974 (Dowbenko et al.) pp. 539–543.

*Primary Examiner*—D. Gabrielle Phelan
*Attorney, Agent, or Firm*—Gary L. Griswold; Walter N. Kirn; John H. Hornickel

[57] ABSTRACT

A crosslinked, acrylate-based pressure-sensitive adhesive is provided to obtain a creep compliance value of the pressure-sensitive adhesive of between $1.1 \times 10^{-5}$ cm$^2$/dyne and $2.3 \times 10^{-5}$ cm$^2$/dyne in the presence of alcohol-based excipients, such as ethanol serving as a solvent or a penetration enhancing agent used with transdermal delivery devices. The method of preparing such crosslinked pressure-sensitive adhesive by using electron beam radiation of from 5 kGy to 200 kGy, and medical articles using the crosslinked pressure-sensitive adhesive as a layer therein to contact skin are also provided.

22 Claims, No Drawings

CROSSLINKED PRESSURE-SENSITIVE ADHESIVES TOLERANT OF ALCOHOL-BASED EXCIPIENTS USED IN TRANSDERMAL DELIVERY DEVICES AND METHOD OF PREPARING SAME

This application is a division of U.S. Ser. No. 07/517,927, filed May 2, 1990, pending.

FIELD OF THE INVENTION

This invention relates to acrylate-based pressure-sensitive adhesives crosslinked by electron beam radiation to become tolerant of alcohol-based excipients such as penetration enhancing agents used in transdermal delivery devices.

BACKGROUND OF THE INVENTION

Pressure-sensitive adhesive tapes have been used for more than half a century for a variety of marking, holding, protecting, sealing, and masking purposes. The earliest medical applications where the product was referred to as an adhesive plaster were not pressure-sensitive adhesives. These were, in fact, crude mixtures of natural rubber plasticized and tackified with wood rosin derivatives and turpentine and heavily pigmented with zinc oxide. These tape-like products served their purpose, but with the advent of truly pressure-sensitive adhesives, they were replaced.

The term "pressure-sensitive adhesive" (PSA) has a precise technical definition and has been dealt with extensively in the technical literature, examples of which are Chapter 17 of Houwink and Salomon "Adhesion and Adhesives", Volume 2, Elsevier Publishing Company, 1967, and the "Handbook of Pressure-Sensitive Technology", Second Edition, Edited by Donatas Satas, Van Nostrand Reinhold Company, 1989.

Fundamentally, PSAs require a delicate balance of viscous and elastic properties which result in a 4-fold balance of adhesion, cohesion, stretchiness, and elasticity. In essence, PSA products have sufficient cohesiveness and elasticity so that, despite their aggressive tackiness, they can be handled with the fingers and removed from smooth surfaces without leaving residue.

The difficulty of adhering tape or other devices to the human skin has long been recognized. The irregular and complex surface of the skin presents difficulties in itself and the wide variation in the skin surface from individual to individual and from location to location on the same individual multiply these difficulties.

Adhesives used in applications that contact the skin require clinical testing that supports a claim that the adhesive is hypoallergenic. These clinical studies are used to confirm that the PSA is neither irritating nor sensitizing to skin.

Acrylic PSAs have been used for many years in medical and surgical applications to adhere items to the skin. U.S. Pat. No. 3,121,021 (Copeland) used an acrylic copolymer of the type described in U.S. Pat. No. 2,884,126/RE24,906 (Ulrich) to provide a porous, surgical adhesive tape with very acceptable skin adhesion performance. A disadvantage encountered using some acrylic PSAs was adhesion build, also known as compliance failure, when the acrylic PSA was in contact with the skin for long periods of time.

In U.S. Pat. No. 3,475,363 (Gander), the compliance failure in acrylate PSAs was overcome by employing a crosslinking agent, dimethylaminoethyl methacrylate, to ensure adhesion to the skin without deleterious effects. Other crosslinking agents have been described for the same purpose: U.S. Pat. Nos. 4,693,776 (Krampe et al.) and 4,732,808 (Krampe et al.) both describe a skin adhesive of an acrylic polymer having grafted to the backbone, polymeric moieties having a glass transition temperature greater than about 20° C. and a weight average molecular weight above about 2000, in order to provide an adhesive composition with a creep compliance value of greater than $1.2 \times 10^{-5}$ $cm^2/dyne$. U.S. Pat. No. 3,532,652 (Zang) describes the partial crosslinking of an acrylate polymer with polyisocyanate to overcome weakening of the cohesive strength of the polymer by migration of skin oils and the like into the adhesive.

Compliance failure can also be remedied by crosslinking an acrylate PSA with a mono-ethylenically unsaturated aromatic ketone monomer using ultra-violet radiation, as described in U.S. Pat. No. 4,737,559 (Kellen et al.). While such ultra-violet irradiation of a crosslinking agent with an acrylate PSA in the presence of a photoinitiator may be useful for some medical applications, it is not useful for medical devices which have a component, e.g. a drug, with the potential of interaction with any residual unreacted photoinitiator, crosslinking agent, or detrimental byproducts of the ultra-violet radiation exposure.

One type of medical device having components which may be susceptible to deleterious interaction is a transdermal delivery device having among other components, a pressure-sensitive adhesive layer and an active agent to be released under controlled conditions to and through the surface of the skin. In U.S. Pat. No. 4,714,655 (Bordoloi et al.), a heat-sensitive material, such as medicaments, fragrances, or repellants, is mixed with a fluid pre-polymer and subjected to ultra-violet radiation, electron beam radiation, or a combination thereof to achieve chain extension and/or crosslinking polymerization, in order to achieve a pressure-sensitive adhesive having the heat-sensitive material entrained therein to yield a transdermal delivery system known as drug-in-adhesive.

Other types of transdermal delivery devices provide multiple-layered constructions where the pressure-sensitive adhesive layer is between the skin and the active agent, typically a pharmaceutical potentially susceptible to processing conditions and potentially reactive with other compounds. Thus, the components in the transdermal delivery device must be inert to the active agent and must be free of unreacted raw materials, by-products and the like which are common to both chemical crosslinking and ultra-violet photoinitiated crosslinking of acrylic PSA's.

Further, the number of active agents suitable for transdermal delivery devices is restricted by the inability of molecules with either (a) a molecular weight too high, or (b) a solubility profile not compatible with the skin structure, to permeate the skin at an acceptable rate for optimal therapeutic blood levels. Therefore, the active agent is often formulated with an excipient, such as a penetration enhancing agent, at a concentration that enables the drug to permeate the skin at the targeted permeation rate and achieve therapeutic blood levels.

Incorporation of penetration enhancing agents in a transdermal device has led to failure of the physical integrity of the construction of the device. Penetration enhancing agents are used in conjunction with the drug to enable the drug to flow through the skin. The transdermal delivery device is often constructed in such a manner that the penetration enhancing agent comes into contact with the pressure sensitive adhesive. The physical properties of the pressure sensitive adhesive can change due to the possible plasticization of the pressure sensitive adhesive by the penetration enhancing agent. The alteration of physical properties can result in delamination of the transdermal delivery device construction, cohesive failure of the pressure sensitive adhesive, and other losses of the ideal physical properties required for a skin adhesive during the course of its storage and usage.

In addition to penetration enhancing agents, other excipients, including alcohol-based drug excipients, are often used with a pharmaceutical for formulation processing, dilution, or other handling reasons. These excipients also can come into contact with the pressure sensitive adhesive with similar potential for alteration of physical properties and similar potential for causing deleterious results for the transdermal device.

Specifically formulated or processed pressure-sensitive adhesives used for a variety of purposes not involving active agents like pharmaceuticals have been known to be resistant to solvents. U.S. Pat. No. 2,973,286 (Ulrich) employed benzoyl peroxide or other organic peroxides to resist the effects of solvents affecting the manufacture of PSA industrial tapes. U.S. Pat. No. 2,925,174 (Stow) provided improved solvent resistance by reaction with liquid epoxy resins and with 2-ethylhexane diol-1,3 for pressure-sensitive adhesive tapes. U.S. Pat. No. 2,956,904 (Hendricks) describes approximately doubling the cohesive strength of pressure-sensitive adhesive used for electrical tapes by high-energy electron beam irradiation such that the crosslinked elastomers were no longer dispersible in the solvents used in coating the adhesive layer on the carrier web or in other common solvents.

Electron beam curing of other pressure-sensitive adhesives to provide solvent resistance has also been described in U.S. Pat. No. 4,695,604 (Amirsakis) for polyurethane resins; in U.S. Pat. No. 4,432,848 (Korpman) for an A-B-A block copolymer, where A represents a poly(monoalkenylarene) block and where B represents a polyisoprene block; in "Formulating to Enhance the Radiation Crosslinking of Thermal Plastic Rubber for Hot Melt Pressure-Sensitive Adhesives", (Ewins, Jr. and Erickson, *Tappi Journal*, June, 1988, pages 155–158), describing styrene-isoprene-styrene polymers crosslinked with electron beam radiation; and in PCT Patent Publication WO 89/00106 (Plamthottam et al.) for double-coated acrylic and rubber based pressure sensitive adhesive foam-like tapes.

Further, U.S. Pat. Nos. 4,699,146 and 4,750,482 describe a hydrophilic pressure-sensitive adhesive produced by ionizing radiation.

What is lacking in the art is a transdermal delivery device pressure-sensitive adhesive which is tolerant of excipients, such as penetration enhancing agents used in conjunction with the active agent being delivered at a rate through the device to the skin that achieves a therapeutic level.

While certain advances have been made in the minimizing compliance failure for skin PSA's, none have succeeded without employing chemical crosslinking agents alone or in combination with ultra-violet radiation initiated polymerization.

While other pressure-sensitive adhesives have been rendered solvent resistant through electron beam radiation, none of those pressure-sensitive adhesives have been used or contemplated for use in a device, having an active agent and its excipients, where that device is to be maintained in adhesive contact with human skin.

While transdermal delivery systems have been described which use electron beam radiation for polymerization of a liquid pre-polymer into a pressure-sensitive adhesive, the transdermal delivery system described therein does not employ the penetration enhancing agents now often used or desired to be used in transdermal delivery devices.

Thus, what is needed in the art of transdermal delivery devices is a hypoallergenic pressure-sensitive adhesive which is unreactive with the active agent to be delivered to the skin and which is tolerant of penetration enhancing agents and other excipients used with the active agent, such that there is no effective compliance failure of the pressure-sensitive adhesive during storage and usage.

SUMMARY OF THE INVENTION

The present invention solves the problems existing in the art of transdermal delivery devices by providing a crosslinked, hypoallergenic pressure-sensitive adhesive (PSA). The crosslinked PSA is prepared from an acrylate-based pressure-sensitive adhesive copolymer having an inherent viscosity between about 1.2 dl/g to about 2.0 dl/g. That copolymer is crosslinked by electron beam radiation of from about 5 kGy to about 200 kGy. After crosslinking, the crosslinked PSA has a creep compliance value of from about $1.1 \times 10^{-5}$ $cm^2$/dyne to about $2.3 \ 10^{-5}$ $cm^2$/dyne notwithstanding exposure to alcohol-based excipients, such as penetration enhancing agents, used or desired to be used with active agents in transdermal delivery devices.

In this description, reference to "pressure-sensitive adhesive copolymer" means the acrylate-based copolymer has not been crosslinked through exposure to electron beam radiation. By contrast, reference in this description to "crosslinked PSA" means the acrylate-based copolymer has been subjected to the desired dose of electron beam radiation.

Therefore, it is an object of the invention to utilize an acrylate-based pressure-sensitive adhesive copolymer and subject it to electron beam radiation, which does not require the photoinitiators needed for ultra-violet polymerization nor the activators or catalysts needed for chemical crosslinking.

It is another object of the invention to use an acrylate-based pressure-sensitive adhesive copolymer which has an inherent viscosity of from about 1.2 dl/g to about 2.0 dl/g prior to crosslinking by electron-beam irradiation in order to provide a crosslinked PSA having a creep compliance value within the range of about $1.1 \times 10^{-5}$ $cm^2$/dyne to about $2.3 \times 10^{-5}$ $cm^2$/dyne which is acceptable for use as a hypoallergenic skin adhesive.

It is another object of the invention to provide a crosslinked PSA that is tolerant of alcohol-based excipients, including penetration enhancing agents such as ethanol, to the extent that preferred adhesive properties represented by a range of creep compliance values remain after exposure to such alcohol-based excipients in a transdermal delivery device.

It is another object of the invention to provide a method for crosslinking a previously polymerized pressure-sensitive adhesive copolymer with electron-beam radiation in a manner which minimizes introduction of undesirable by-products of chemical or photochemical reaction into the resulting crosslinked PSA and minimizes retention of unreacted raw materials in the resulting crosslinked PSA. Such a crosslinking method minimizes interaction of such by-products or raw materials with an active agent present in the transdermal delivery device.

It is another object of the invention to provide a transdermal delivery device having a crosslinked PSA layer which is tolerant of alcohol-based excipients useful for the delivery of active agents to the skin to which the crosslinked PSA is adhered.

These and other objects of the invention are achieved by polymerizing an acrylate-based polymerizable monomer and an ethylenically unsaturated monomer in a weight fraction ratio of the acrylate-based polymerizable monomer to the ethylenically unsaturated monomer of from about 92:8 to about 98:2 to yield a pressure-sensitive adhesive copolymer having an inherent viscosity of from about 1.2 dl/g to about 2.0 dl/g, followed by irradiating that pressure-sensitive adhesive copolymer with an electron-beam radiation dose of from about 5 kGy to about 200 kGy to yield a crosslinked PSA having a creep compliance value of from about $1.1 \times 10^{-5}$ $cm^2/dyne$ to about $2.3 \times 10^{-5}$ $cm^2/dyne$ even after exposure to alcohol-based excipients used with an active agent in a transdermal delivery device.

The invention is also achieved by an acrylate-based crosslinked PSA having such properties and so prepared.

The invention is also achieved by providing a transdermal delivery device comprising a acrylate-based crosslinked PSA layer so prepared and a therapeutic mixture in contact with and often deliverable through the crosslinked PSA layer, the mixture comprising a transdermally therapeutic active agent and an alcohol-based excipient.

An advantage of the present invention is the acrylate-based crosslinked PSA maintains acceptable skin adhesion properties represented by a range of creep compliance values after electron-beam irradiation and even after exposure to alcohol-based excipients in weight/weight concentrations of as much as 10 percent of the crosslinked PSA for as long as is needed for product stability during storage and usage.

"Creep compliance value", also known as "J value", is a measure of a fundamental rheological property of pressure-sensitive adhesives. The fundamentals of creep compliance as they relate to polymeric materials and in particular viscoelastic polymers are described in the following publications: (1) "Viscoelastic Properties of Polymers", John D. Ferry, Third Edition, John Wiley & Sons, 1980, Chapter 1; (2) "Treatise on Adhesion and Adhesives", Volume 2, "Materials", Pressure-Sensitive Adhesives, R. L. Patrick, Editor, Marcel Dekker, Inc., 1969; (3) "Properties and Structure of Polymers", Tobolsky, John Wiley & Sons, 1960, Chapter II, Section 6, wherein the five regions of viscoelastic behavior are discussed; and (4) C. A. Dahlquist writing in "Handbook of Pressure-Sensitive Adhesive Technology", edited by Donatas Satas, Van Nostrand Reinhold Company, Second Edition, 1989, Chapter 5, wherein it is described that the stress-strain behavior of pressure sensitive adhesives can be treated as a creep compliance phenomenon.

For purpose of the present invention, a range of creep compliance values has been found to be useful in presenting a quantitative determination of preferred skin adhesion properties for the crosslinked PSA.

Because adhesion to human skin is most difficult to measure and no synthetic material adequately simulates human skin when testing for skin adhesion, creep compliance values serve to correlate an adhesive physical property to the qualitative assessment of acceptable skin adhesion. For example, a creep compliance value of greater than about $2.3 \times 10^{-5}$ $cm^2/dyne$ would correlate to a qualitative assessment that the pressure sensitive adhesive skin adhesion is too "gooey." On the other hand, a creep compliance value of less than about $1.1 \times 10^{-5}$ $cm^2/dyne$ would correlate to a qualitative assessment that the pressure sensitive adhesive skin adhesion is too "stiff."

Pressure sensitive adhesives having a creep compliance value between $1.1 \times 10^{-5}$ $cm^2/dyne$ and $2.3 \times 10^{-5}$ $cm^2/dyne$ provide an acceptable level of initial adhesion to skin and sufficiently maintain adhesive integrity during storage and usage, without cohesive failure or adhesion loss. The crosslinked PSAs of the present invention maintain such physical properties even when in contact with alcohol-based excipients otherwise harmful to such physical properties.

Additional aspects of the invention are described in Embodiments of the Invention below, including non-limiting examples.

Embodiments of the Invention

THE PRESSURE-SENSITIVE ADHESIVE COPOLYMER

The pressure-sensitive adhesive copolymer is an acrylate-based and has an inherent viscosity of from about 1.2 dl/g to about 2.0 dl/g. Desirably, the inherent viscosity ranges from about 1.4 dl/g to about 1.9 dl/g in order to provide a creep compliance value within the acceptable range after the copolymer is irradiated with a dose of electron-beam radiation and exposed to alcohol-based excipients. Preferably, the inherent viscosity is about 1.7 dl/g.

Inherent viscosity is a logarithmic viscosity number used to measure polymer molecular weight for linear polymers. The test procedure followed and the apparatus that can be used to measure inherent viscosity are described in detail in Testing Procedures below.

The pressure-sensitive adhesive copolymer should be tacky at room temperature as well as at the skin temperature of patients. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Administration recommends such evaluations in a Tripartite Biocompatibility Draft Guidance for Medical Devices.

The acrylate-based pressure-sensitive adhesive copolymer is the reaction product of the polymerization of at least one A monomer and at least one B monomer.

The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms.

The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof.

The A monomer is polymerizable and contributes the viscoelastic properties of the pressure-sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commerically available.

The B monomer is an ethylenically unsaturated compound copolymerized with the A monomer to affect the physical properties of the resulting pressure-sensitive adhesive copolymer. In general, the presence of the B monomer will reduce the flexibility of the resulting pressure-sensitive adhesive copolymer.

Thus, the weight percentages of the A monomer and the B monomer should be balanced in order to provide a pressure-sensitive adhesive copolymer having an inherent viscosity of from about 1.2 dl/g to about 2.0 dl/g. The weight percentage ratio ranges from about 92:8 to about 98:2 and desirably from about 93:7 to 97:3.

In a preferred embodiment of the invention, the pressure-sensitive adhesive copolymer is the reaction product of isooctyl acrylate and acrylic acid having a weight percentage ratio of from about 92:8 to about 97:3 and preferably having a weight percentage ratio of about 95.5:4.5.

The pressure-sensitive adhesive copolymer may be copolymerized using known polymerization techniques in a manner such that the inherent viscosity of the resulting copolymer is from about 1.2 dl/g to about 2.0 dl/g. Known polymerization techniques include emulsion polymerization and solution polymerization. Sources of polymerization preparation and techniques include "Organic Polymer Chemistry", K. J. Saunders, Chapman and Hall (Halsted Publishing, New York, 1973), Applied Polymer Science, R. W. Tess and G. W. Poehlein, American Chemical Society (Amercian Chemical Society, Washington, D.C., 1981), Principles of Polymerization, G. Odien, Wiley-InterScience (John Wiley & Sons, New York, 1981), and the Handbook of Pressure-Sensitive Adhesive Technology, Second Edition, referenced above, the disclosures of which are incorporated by reference.

Specifically, the acrylate-based pressure-sensitive adhesive copolymers may be prepared according to U.S. Pat. No. 2,884,126/RE24,906, the disclosure of which is incorporated herein by reference.

When prepared by solution copolymerization, the A monomer and B monomer are dissolved in an inert organic solvent and copolymerized in a nitrogen purged reactor at a temperature of about 55° C. for about 24 hours using a suitable free radical initiator, such as azobisisobutyronitrile. Suitable solvents include ethyl acetate, mixtures of ethyl acetate and ethanol, and n-heptane.

When prepared by emulsion copolymerization, the A monomer and B monomer are dispersed in deionized water using the procedure described in Example 5 of U.S. Pat. No. 2,884,126/RE24,906, except that the amount of tertiary dodecyl mercaptan may be varied to provide copolymers having a range of inherent viscosities, and that the resulting copolymer is dissolved in a heptane-isopropanol (70:30) solution.

THE CROSSLINKED PSA

The pressure-sensitive adhesive copolymer may be crosslinked using electron-beam radiation in doses of from about 5 kGy (0.5 Mrads.) to about 200 kGy (20 Mrads.). Desirably, the electron-beam radiation dose is from about 10 kGy to about 50 kGy and may be delivered using one pass or multiple passes through the electron beam.

In a preferred embodiment of the invention, when the pressure-sensitive adhesive copolymer is prepared from the copolymerization of isooctyl acrylate and acrylic acid, electron-beam radiation in a dose of about 30 kGy yields an acceptable crosslinked PSA for use in a transdermal delivery device.

The method of irradiation by electron-beam is performed by passing the pressure-sensitive adhesive copolymer on suitable substrates through an electron beam unit as available from Energy Sciences Inc., such as a Model CB 250/30/20 30 cm Electro-Curtain electron beam system or a Model CB 150/15/10L 15 cm Electro-Curtain electron beam system, configured to operate and provide the acceptable dosages indicated above. In the embodiment of providing a dose of 30 kGy of electron-beam radiation, the equipment is operated at a voltage of 175 kV at a line speed of 15.24 meters per minute with an oxygen content of less than 100 parts per million.

The electron-beam radiation results in crosslinking the pressure-sensitive adhesive copolymer without otherwise affecting the pressure-sensitive adhesive properties useful for medical applications.

TESTING PROCEDURES

Inherent Viscosity Measurement Procedure

The inherent viscosities of the pressure sensitive adhesive copolymers were obtained using a Cannon-Fenske #50 viscometer in a deionized water bath controlled at 25° C. to measure the flow time of 10 ml of the copolymer solution (0.15 g/dl of copolymer in ethyl acetate.) The test procedure followed and a drawing of a viscometer, then known as a Ostwald-Fenske, are described in "Textbook of Polymer Science", F. W. Billmeyer, Wiley-Interscience, Second Edition, 1971, Pages 84 and 85, the disclosure of which is incorporated by reference.

Creep Compliance Value Procedure

To measure the creep compliance value of the skin adhesive pressure-sensitive adhesive copolymer before crosslinking, after crosslinking, and after crosslinking and exposure to the penetration enhancing agents, a 150-micrometer thickness of the pressure-sensitive adhesive copolymer is knife-coated onto a smooth film of polytetrafluoroethylene. The coated film is then dried to a constant weight by placing it in an air-circulating oven for at least 30 minutes at 65° C. to remove solvent and reduce the level of unreacted monomer.

The adhesive, thus dried, is stripped from the polytetrafluoroethylene and two test pieces of equal area are die-cut and placed in the parallel plate creep compliance rheometer, one piece being on each side of the center plate, with an outer plate contacting the exposed surface of each. Screws which connect the two outer plates are then tightened so as to compress the interposed layers of adhesive approximately 10 percent. The parallel plates are placed in a horizontal arrangement and one end of the center plate is connected to a chart recorder. A hook is attached to the opposite end of the center plate with a flexible wire extending horizontally from the hook and then downward over a pulley, the outer plates being held in a fixed position. A suitable weight (one sufficient to measurably deform the sample at distance no greater than its thickness) is attached to the free end of the wire, then the strip chart recorder is started. The weight typically used to exert the stress on the adhesive films is about 500 grams. From the strip chart recorder, the time and displacement (strain) are read and the applied force (stress) is recorded. The creep compliance at a given temperature is then calculated using the equation:

$$J_{(t)} = \frac{2AX}{hf}$$

where t is the time at which the measurement is taken, A is the area of one face of the adhesive samples, h is the thickness of the adhesive mass, X is the displacement at time t (where X is less than h) and f is the force due to the mass attached to the wire connected to the middle plate. When A is expressed in cm², h in centimeters, X in centimeters, and f in dynes, the compliance value or J value, $J_{(t)}$ is given in cm²/dyne.

When the creep compliance value has been measured at the end of a 3 minute period of stress application according to the procedure described above, a pressure-sensitive adhesive having a creep compliance value of from about $1.1 \times 10^{-5}$ cm²/dyne to about $2.3 \times 10^{-5}$ cm²/dyne exhibits acceptable adhesion to skin.

In general, the higher the creep compliance value, the lower the cohesiveness of the pressure-sensitive adhesive and the higher the adhesion level to the skin. For a pressure-sensitive adhesive having a creep compliance value higher than about $2.3 \times 10^{-5}$ cm²/dyne, the pressure-sensitive adhesive has a higher adhesion with lower internal or cohesive strength, resulting in excessive residue remaining on the skin at the time of adhesive removal. When the value is less than about $1.1 \times 10^{-5}$ cm²/dyne, the pressure-sensitive adhesive exhibits lower tack and higher cohesive strength, resulting in poor initial adhesion.

Skin Adhesion Procedure

The evaluation of the skin adhesives of this invention is highly subjective when the performance in contact with and upon removal from the human skin surface becomes part of the evaluation. For this reason a protocol was developed using a prescribed test panel of individuals who were selected to embrace the normal variations in skin surface that are encountered in medical practice. The result of this designed study enables one to get values which can be considered controlled and comparative. While these values are observational in respect to adhesive residue, sample lift and adhesion build-up, the procedures followed are in accord with carefully developed assessments of similar properties as is known in the art.

It should be noted that there is an inherent variability in skin adhesion between different individuals and for the same individual, depending in each instance on the type of skin, the time of the year, the climatic conditions, the level of exercise, and other factors. Thus, while certain values are reported here, there are wide ranges of adhesion values possible due to other factors in actual usage.

The initial skin adhesion value ($T_0$) and the skin adhesion value after 24 or 48 hours in contact with the skin ($T_{24}$ or $T_{48}$) are essentially the widely accepted PSTC-1, peel adhesion test for single coated skin adhesive tapes measured at 180° angle. PSTC-1 is test method No. 1 of the Pressure Sensitive Tape Counsel, Glenview, Ill., Seventh Edition (1976); developed by the Specifications and Technical Committee of the Counsel. The test has been modified only to the extent that the tape is applied to the human skin surface on a selected area on the individual's back. Otherwise the steps in the procedure are as follows:

1. Tape samples 2.54 cm wide by 5.08 cm long are placed on the back of a human subject.
2. Each tape is rolled down with one forward and one reverse pass, using a 1-kilogram tape roller (described in Appendix B, Sections 2.7.1, 2.8.1, and 2.8.2 of Pressure Sensitive Tape Counsel) moved at the rate of about 30 cm per minute.
3. Adhesion to the skin is measured as the peel force required to remove the tape at 180° angle (PSTC-1). The peel force values are measured through the use of a strain-gauge mounted on a motor-driven carriage. The force of removal is reported in grams of adhesion per 2.54 cm of width of sample. The rate of removal is 15 cm per minute.
4. The adhesion to skin is measured immediately after initial application ($T_0$) and after 24 or 48 hours of continuous contact with the skin ($T_{24}$ or $T_{48}$). Preferred skin adhesive will generally exhibit a $T_0$ of between 50 grams to about 200 grams and a $T_{24}$ of between 50 grams and 200 grams.

EXCIPIENT EXPOSURE PROCEDURE

To measure the effect of the exposure of the pressure-sensitive adhesive copolymer and the crosslinked PSA to the alcohol-based excipient, samples of the copolymer and the crosslinked PSA were sprayed with ethanol, a frequently used penetration enhancing agent and solvent excipient. The ethanol is sprayed either in a series of five sprays at a distance of 15.24 cm or in a single spray at a distance of 25.4 cm. After hand-laminating the sample exposed to ethanol to a sample not exposed to ethanol, these samples were allowed to dwell at room temperature for five days before the creep compliance procedure was performed. Care should be taken during hand-lamination not to introduce air-pockets, lint, or any other contaminants. Some ethanol may flow from the samples having five sprays during hand-lamination. It is believed that the procedure of five sprays at a distance of 15.24 cm provides a 10 percent weight/weight amount of ethanol in the pressure-sensitive adhesive whereas a single coating spray at 25.4 cm provides a 5 percent weight/weight amount of ethanol in the pressure-sensitive adhesive.

ALCOHOL-BASED EXCIPIENT EXPOSURE

A comparison of identically prepared pressure-sensitive adhesive samples demonstrates that electron-beam irradiation in specific dosages unexpectedly results in a crosslinked PSA which maintains its creep compliance value within an acceptable range after exposure to ethanol.

With a pressure-sensitive adhesive copolymer having an inherent viscosity of from about 1.2 dl/g to about 2.0 dl/g, the creep compliance value before exposure to ethanol may be within the acceptable range of about $1.1 \times 10^{-5}$ cm²/dyne to about $2.3 \times 10^{-5}$ cm²/dyne.

Without electron-beam irradiation of the pressure-sensitive adhesive copolymer, after exposure to ethanol, only the pressure-sensitive adhesive copolymer samples having the highest inherent viscosity in the acceptable range retain a creep compliance value below about $2.3 \times 10^{-5}$ cm²/dyne. The remaining samples of pressure-sensitive adhesive copolymer exceed the acceptable range of creep compliance value and demonstrate dramatic loss of cohesive strength.

Unexpectedly, after samples of the pressure-sensitive adhesive copolymer having an inherent viscosity within the acceptable range are irradiated with an electron-beam, the creep compliance values for the samples remain within the acceptable range even after exposure for as much as 5 days to the presence of ethanol in weight fractions as much as 10 percent weight/weight to the PSA.

Because the electron-beam irradiation of the pressure-sensitive adhesive copolymer causes retention of the cohesive strength of the crosslinked PSA in the presence of a penetration enhancing agent, it is also possible within the scope of this invention to begin with a pressure-sensitive adhesive copolymer having a creep compliance value less than about $1.1 \times 10^{-5}$ cm²/dyne. After irradiation, this adhesive may be used in a transdermal delivery device having an alcohol-based excipient, such as a penetration enhancing agent, such that after exposure to such excipient, the crosslinked PSA layer has a creep compliance value lower than about $2.3 \times 10^{-5}$ cm²/dyne.

It should be understood from this invention that one skilled in the art can select a pressure-sensitive adhesive copolymer having otherwise acceptable skin adhesion properties, and subject that copolymer to electron-beam radiation to produce a crosslinked PSA which has acceptable skin adhesion properties even in the presence of a specific alcohol-based excipient which otherwise would decrease the cohesive strength of the un-crosslinked pressure-sensitive adhesive copolymer.

USEFULNESS OF THE INVENTION

As described above, the crosslinked PSA may be used as the adhesive layer in a transdermal delivery device in a medical or surgical application. In other circumstances where skin adhesion stability is desired, medical applications such as dressings, bandages, drapes, and the like may be improved by use of the crosslinked PSA's of this invention. Regardless of the medical application, the product can have an extended shelf life even if the crosslinked PSA is in contact with an alcohol-based excipient, including penetration enhancing agents like ethanol. Further, the maintenance of creep compliance values within the acceptable range reduces the likelihood of a painful removal of the medical article due to lower build of adhesion of the crosslinked PSA during extended use. The number of excipients used with a therapeutic agent and especially those penetration enhancing agents available for use with the acrylate-based pressure-sensitive adhesive may now be expanded because of the tolerance of the crosslinked PSA to such alcohol-based materials. More importantly, the range of active agents that can be administered transdermally can now be expanded to include those which must use an alcohol-based excipient as a solvent or penetration enhancing agent.

Non-limiting examples of alcohol-based excipients of which the crosslinked PSA's of this invention are tolerant include ethanol, octanol, eugenol, and any N-alkanol, branched alkanol, or cyclic alkanol. Other alcohol-based excipients are alcohol-based penetration enhancing agents known to those skilled in the art, as disclosed in U.S. Pat. Nos. 4,849,224 and 4,855,294, the disclosures of which are incorporated herein by reference.

Non-limiting examples of active agents useful in a transdermal delivery device with such alcohol-based excipients as solvents, penetration enhancing agents and the like, are estradiol, nicotine, nitroglycerine, clonidine, and scopolamine. Other active agents are identified as drugs or pharmacologically active agents and are also disclosed in U.S. Pat. Nos. 4,849,224 and 4,855,294.

One type of transdermal delivery device typically places the pressure sensitive adhesive against the skin with a reservoir of a therapeutic mixture in communication therewith. The therapeutic mixture comprising the active agent and the alcohol-based excipient is deliverable through the crosslined PSA layer according to the natural flow of the therapeutic mixture, or using rate controlling membranes or the like.

Another type of transdermal delivery device places the pressure sensitive adhesive contiguous with, but not between, the reservoir containing the therapeutic mixture and the skin. For example, a construction where the adhesive is about a periphery of the reservoir is often employed in the art.

Either type of transdermal delivery device has contact between the alcohol-based excipient and the pressure sensitive adhesive. The crosslinked PSA's of the present invention minimize loss of preferred adhesive properties when used in either type of transdermal delivery device.

Because the pressure-sensitive adhesive copolymer is crosslinked by electron-beam radiation without the use of crosslinking agents, initiators, or the like, the number of materials with which the active agent may interact is minimized. With the benefit of this invention, one skilled in the art can refine the skin adhesion properties of the crosslinked PSA layer without affecting the transport of the active agent through the PSA layer and into the skin. Indeed, the number of active agents available for transdermal delivery can now be expanded for use with alcohol-based excipients serving as solvents or penetration enhancing agents that no longer cause cohesive failure of the crosslinked PSA layer necessary to hold the transdermal delivery device together or to the skin.

For a greater appreciation of the scope of the invention, non-limiting examples are provided.

EXAMPLES 1–5

Preparation of the Pressure-Sensitive Adhesive Copolymer Having a Range of Inherent Viscosities A series of acrylate-based pressure-sensitive adhesive copolymers were prepared by emulsion polymerization, described as follows: A mixture of 104 parts by weight of deionized water, 8 parts of a 28% solution of alkylated aryl polyether sodium sulfonate ("Triton X-200" sold by Rohm and Haas), 95.5 parts of isooctyl acrylate, 4.5 parts acrylic acid and amounts tertiary dodecyl mercaptan described below to vary inherent viscosity was purged with nitrogen and brought to 30° C. with agitation. To this were added 0.2 parts potassium persulfate and 0.067 parts sodium metabisulphite. Copolymerization proceeded rapidly with evolution of heat. The copolymer was recovered from the emulsion, dried, and dispersed in a mixture of heptane/isopropanol (70/30) to a coatable viscosity. Inherent viscosities were measured using the Inherent Viscosity Procedure described above in ethyl acetate at a concentration of 0.15 g/dl. To yield a series of copolymers having a range of inherent viscosities from about 1.0 dl/g to about 2.0 dl/g, for Examples 1–5, respectively, in weight percent to total monomer weight, the amount of tertiary dodecyl mercaptan added was 0.13% for Example 1, 0.11% for Example 2, 0.07% for Example 3, 0.06% for Example 4, and none for Example 5. The samples of copolymer were hand-spread on a 15.24 cm coater at a nominal 4.6 mg/cm² (11 grain) coverage on a 0.05 mm untreated polyester film. These samples were then covered with a paper liner available as No. 1361 from 3M Company.

EXAMPLES 6–10

Crosslinking by Electron-Beam Irradiation

Copolymer samples of Examples 1–5 were then irradiated with an electron beam to yield crosslinked PSA samples of Examples 6–10. The Examples 6–10 correspond to Examples 1–5, respectively, except for the electron-beam radiation crosslinking. Each of the copolymer samples were irradiated with an electron-beam on an Energy Sciences Inc. "ESI Model CB 250/30/20" 30 cm Electro-Curtain electron beam unit operating at a voltage of 175 kV at a line speed of 15.24 meters per minute having an oxygen content of less than 100 parts per million to achieve an electron-beam dosage of 30 kGy (3.0 Mrads.)

Exposure to Ethanol

Portions of adhesive prepared according to the procedures used for each of Examples 1–10, each approximately 500 cm$^2$ in size, were exposed to ethanol (100%) according to single spray and 5-spray variations of the Excipient Exposure Procedure described above. Other samples of Examples 1–10 were not exposed to ethanol. During laminating, some ethanol of the 5-spray samples was pressed out. The ethanol exposed samples were stored at room temperature for 5 days prior to performing the creep compliance procedure. It was believed that the single spray procedure added about 5 percent (w/w) ethanol to the sample and the 5-spray procedure added 10 percent (w/w) ethanol to the sample.

The creep compliance procedure described above was performed for 10 samples each of Examples 1–10 under three conditions: unexposed to ethanol, exposed to ethanol at about 5 percent, and exposed to ethanol at about 10 percent. Table I demonstrates the results obtained for an average of the samples.

TABLE I

| Example | Inherent Viscosity (dl/g) | Electron-Beam Dosage (kGy) | Creep Compliance ($\times 10^{-5}$ cm$^2$/dyne) Ethanol % (w/w) | | |
|---|---|---|---|---|---|
| | | | 0% | 5% | 10% |
| 1 | 1.02 | 0 | 2.348 | 6.414 | 6.053 |
| 2 | 1.16 | 0 | 2.142 | 3.839 | 5.167 |
| 3 | 1.44 | 0 | 1.695 | 2.295 | 5.384 |
| 4 | 1.69 | 0 | 1.520 | 1.602 | 3.788 |
| 5 | 1.94 | 0 | 1.250 | 1.824 | 2.179 |
| 6 | 1.02 | 30 | 3.766 | 3.566 | 4.015 |
| 7 | 1.16 | 30 | 1.405 | 2.518 | 2.953 |
| 8 | 1.44 | 30 | 1.140 | 1.538 | 2.066 |
| 9 | 1.69 | 30 | 1.390 | 1.650 | 1.787 |
| 10 | 1.94 | 30 | 1.170 | 1.620 | 2.305 |

The underscored creep compliance values in Table I are in the acceptable range for skin-adhesion performance of a pressure-sensitive adhesive. Referring to Examples 1, 2, 6, and 7, notwithstanding the crosslinking by the electron-beam irradiation, the creep compliance values in the presence of ethanol were outside the acceptable range even though the values may be acceptable prior to exposure to ethanol. Therefore, the initial inherent viscosity of the pressure-sensitive adhesive copolymer should be between about 1.2 dl/g and about 2.0 dl/g.

A comparison of Examples 3 and 4 with Examples 8 and 9, respectively, shows the benefit of crosslinking using the electron-beam irradiation. While some exposure to ethanol can be tolerated in Examples 3 and 4, cohesive strength of the copolymers in Examples 3 and 4 is lost upon 10 percent ethanol exposure. On the other hand, with electron-beam irradiation of the same pressure-sensitive adhesive copolymers, the creep compliance values of the crosslinked PSA's of Examples 8 and 9 are within the acceptable range despite exposure to ethanol in either amount.

A comparison of Examples 5 and 10 shows that at the upper boundary of the inherent viscosity range, it is possible to provide tolerance to ethanol at the levels of ethanol exposure tested even though crosslinking may initially depress the creep compliance value such that it approaches the lower boundary of the acceptable range prior to exposure to ethanol. Even with a pressure-sensitive adhesive copolymer having a high inherent viscosity of greater than 1.90, it is preferable to crosslink the copolymer to form the the crosslinked PSA to assure a creep compliance value within the acceptable range. This is an example of the selection available to one skilled in the art to "fine tune" the pressure-sensitive adhesive properties in a transdermal delivery device when it is known that an alcohol-based excipient will be present.

EXAMPLES 11–13

Examples 11–13 were prepared from IOA/AA (95.5:4.5) copolymers prepared according to the procedure described with respect to Examples 1–5, using 0.05% to 0.07% of monomer weight of tertiary dodecyl mercaptan to yield an inherent viscosity in the range of 1.4 dl/g to 1.6 dl/g. The samples of Example 11 were not irradiated. The samples of Example 12 were irradiated with an electron-beam dosage of 30 kGy in one pass in the ESI electron beam unit. The samples of Example 13 were irradiated three times with a dosage of 10 kGy during each pass.

Samples of each of the three examples were prepared according to the skin adhesion procedure described above and tested on human skin surface. Table II reports the results obtained based on an average of the samples.

TABLE II

| Example | Inherent Viscosity (dl/g) | Electron-Beam Dosage (kGy) | Skin Adhesion (g/2.54 cm) | |
|---|---|---|---|---|
| | | | $T_0$ | $T_{24}$ |
| 11 | 1.4–1.6 | 0.0 | 100 | 175 |
| 12 | 1.4–1.6 | 30 | 65 | 85 |
| 13 | 1.4–1.6 | 10 + 10 + 10 | 60 | 90 |

All of the examples were within or close to the preferred range of 50 grams to 200 grams on initial skin adhesion. After 24 hours, the skin adhesion for Example 13 rose although staying within the preferred range of skin adhesion.

Unexpectedly, the increase in skin adhesion for the first 24 hours was dramatically less for Examples 12 and 13 which were exposed to electron-beam radiation. The rate of increase for Examples 12 and 13 compared with Example 11 was lower both on a percentage basis and on an absolute basis. Further, the rate of increase for the crosslinked PSA was not dependent on the method of delivery of the dose of electron-beam radiation.

Thus, while all of the examples show acceptable skin adhesion, the electron-beam crosslinking of pressure-sensitive adhesive copolymers to yield crosslinked PSA's minimizes the increase in skin adhesion over as much as a 24 hour period. This translates into easier removal of the transdermal delivery device or other medical article prepared according to the present invention after its intended purpose on the human skin has been accomplished.

While several embodiments and examples have been provided, the scope of the invention is not limited thereto.

What is claimed is:

1. A method of preparing a pressure sensitive adhesive tolerant of exposure to an alcohol-based excipient used with an active agent for transdermal delivery, comprising:

(a) polymerizing at a temperature of at least about 30° C. in the absence of a therapeutic mixture at least one acrylate-based polymerizable monomer and at least one ethylenically unsaturated monomer in a weight fraction ratio of said acrylate-based polymerizable monomer to said ethylencially unsaturated monomer of from about 92:8 to about 98:2 to yield a pressure sensitive adhesive copolymer having an inherent viscosity of from about 1.2 dl/g to about 2.0 dl/g; and then separately (b) irradiating with an electron beam radiation dose of about 5.0 kGy to about 200 kGy the previously polymerized pressure sensitive adhesive copolymer in the absence of photoinitiators needed for ultra-violet polymerization, activators or catalysts needed for chemical crosslinking, and further in the absence of the active agent or the alcohol-based excipient to yield a radiation crosslinked pressure sensitive adhesive useful in a transdermal delivery device having a creep compliance value of from about $1.1 \times 10^{-5}$ cm$^2$/dyne to about $2.3 \times 10^{-5}$ cm$^2$/dyne after exposure to the alcohol-based excipient.

2. A method according to claim 1, wherein said polymerizing occurs by emulsion polymerization.

3. A method according to claim 1, wherein said polymerizing occurs by solution polymerization.

4. A method according to claim 1, wherein said acrylate-based polymerizable monomer comprises an acrylate or methacrylate ester of a non-tertiary alcohol or a mixture of non-tertiary alcohols, said alcohols having from 1 to 14 carbon atoms with the average number being about 4–12; and wherein said ethylenically unsaturated monomer comprises acrylic acid, methacrylic acid, itaconic acid, acrylamide, methacrylamide, acrylonitrile, methacrylonitirile, vinyl acetate, N-vinylpyrrolidone, or combinations thereof.

5. A method according to claim 4, wherein said acrylate-based polymerizable monomer comprises isooctyl acrylate and wherein said ethylenically unsaturated monomer comprises acrylic acid.

6. A method according to claim 5, wherein said isooctyl acrylate and said acrylic acid have a weight fraction ratio of from about 93:7 to about 97:3.

7. A method according to claim 6, wherein said isooctyl acrylate and said acrylic acid have a weight fraction ratio of about 95.5:4.5.

8. A method according to claim 1, wherein said irradiating is in a dose of from about 10 kGy to about 50 kGy.

9. A method according to claim 8, wherein said irradiating is in a dose of about 30 kGy.

10. A method according to claim 7, wherein said crosslinked pressure sensitive adhesive has said creep compliance value after exposure to ethanol.

11. A method of preparing a pressure sensitive adhesive used for transdermal delivery, comprising:

(a) polymerizing in the absence of a therapeutic mixture at least one acrylate-based polymerizable monomer and at least one ethylenically unsaturated monomer in a weight fraction ratio of said acrylate-based polymerizable monomer to said ethylencially unsaturated monomer of from about 92:8 to about 98:2 to yield a pressure sensitive adhesive copolymer having an inherent viscosity of from about 1.2 dl/g to about 2.0 dl/g; and then separately (b) irradiating said copolymer in the absence of the active agent or the alcohol-based excipient with an electron beam radiation dose of about 5.0 kGy to about 200 kGy to yield a crosslinked pressure sensitive adhesive having a creep compliance value of from about $1.1 \times 10^{-5}$ cm$^2$/dyne to about $2.3 \times 10^{-5}$ cm$^2$/dyne after exposure to the alcohol-based excipient; and then (c) contacting the crosslinked pressure sensitive adhesive with a therapeutic mixture in a transdermal delivery device.

12. The method according to claim 11, wherein said polymerizing occurs by emulsion polymerization.

13. The method according to claim 11, wherein said polymerizing occurs by solution polymerization.

14. The method according to claim 11, wherein said acrylate-based polymerizable monomer comprises an acrylate or methacrylate ester of a non-tertiary alcohol or a mixture of non-tertiary alcohols, said alcohols having from 1 to 14 carbon atoms with the average number being about 4–12; and wherein said ethylenically unsaturated monomer comprises acrylic acid, methacrylic acid, itaconic acid, acrylamide, methacrylamide, acrylonitrile, methacrylonitirile, vinyl acetate, N-vinylpyrrolidone, or combinations thereof.

15. The method according to claim 14, wherein said acrylate-based polymerizable monomer comprises isooctyl acrylate and wherein said ethylenically unsaturated monomer comprises acrylic acid.

16. The method according to claim 15, wherein said isooctyl acrylate and said acrylic acid have a weight fraction ratio of from about 93:7 to about 93:3.

17. The method according to claim 16, wherein said isooctyl acrylate and said acrylic acid have a weight fraction ratio of about 95.5:4.5.

18. The method according to claim 11, wherein said irradiating is in a dose of from about 10 kGy to about 50 kGy.

19. The method according to claim 18, wherein said irradiating is in a dose of about 30 kGy.

20. The method according to claim 19, wherein said crosslinked pressure sensitive adhesive has said creep compliance value after exposure to ethanol.

21. A method of using a pressure sensitive adhesive comprising the steps of:

(a) contacting a crosslinked pressure sensitive adhesive prepared according to claim 1 with a therapeutic mixture in a transdermal delivery device, and (b) adhering the crosslinked pressure sensitive adhesive to skin.

22. A method of using a pressure sensitive adhesive comprising the step of adhering to skin a crosslinked pressure sensitive adhesive according to claim 11.

* * * * *

UNITED STATES PATENT AND TRADEMARK OFFICE
CERTIFICATE OF CORRECTION

PATENT NO. : 5,618,899
DATED : April 8,1997
INVENTOR(S) : Marian R. Appelt and Sharon K. Grosh It is certified that error appears in the above-identified patent and that said Letters Patent is hereby corrected as shown below:

On the title page
Before "[21] Appl. No.: 454,496 " insert --Assignee: Minnesota Mining and Manufacturing Company, St. Paul, Minn.--

Signed and Sealed this

Third Day of February, 1998

Attest:

BRUCE LEHMAN

Attesting Officer

Commissioner of Patents and Trademarks